United States Patent [19]

Hoyles et al.

[11] Patent Number: 5,030,444
[45] Date of Patent: Jul. 9, 1991

[54] PROCESS FOR MAKING TOOTHPASTE

[75] Inventors: Ronald Hoyles, Cheshire; Andrew E. Wilde, Merseyside, both of England

[73] Assignee: Chesebrough-Pond's USA Co., division of Conopco, Inc., Greenwich, Conn.

[21] Appl. No.: 384,855

[22] Filed: Jul. 21, 1989

Related U.S. Application Data

[63] Continuation of Ser. No. 930,461, Nov. 12, 1986, abandoned.

[30] Foreign Application Priority Data

Nov. 14, 1985 [GB] United Kingdom ............... 8528117

[51] Int. Cl.$^5$ .......................... A61K 7/16; B01J 13/00
[52] U.S. Cl. ..................................... 424/49; 252/314; 252/315.3; 424/52; 424/499; 424/500; 514/777; 514/782
[58] Field of Search .................. 252/315.3; 424/49, 52

[56] References Cited

U.S. PATENT DOCUMENTS

| | | | |
|---|---|---|---|
| 3,840,657 | 10/1974 | Norfleet | 424/49 |
| 4,144,322 | 3/1979 | Cordon et al. | 424/49 |
| 4,348,378 | 9/1982 | Kosti | 424/49 X |
| 4,349,534 | 9/1982 | Eigen et al. | 424/49 |
| 4,374,823 | 2/1983 | Harvey et al. | 424/49 X |
| 4,401,648 | 8/1983 | Piechota | 424/49 |
| 4,599,363 | 7/1986 | Miles et al. | 424/49 |
| 4,701,319 | 10/1987 | Woo | 424/49 X |
| 4,795,630 | 1/1989 | Okouchi et al. | 424/49 |

FOREIGN PATENT DOCUMENTS

| | | |
|---|---|---|
| 30435 | 6/1981 | European Pat. Off. |
| 2344962 | 3/1975 | Fed. Rep. of Germany |
| 1434087 | 4/1976 | United Kingdom |
| 1604215 | 12/1981 | United Kingdom |
| 1604216 | 12/1981 | United Kingdom |
| 2082062 | 3/1982 | United Kingdom ............ 424/49 |
| 2117637 | 10/1983 | United Kingdom |
| 2082062B | 7/1984 | United Kingdom |

OTHER PUBLICATIONS

"Soap, Cosmetics Chemical Specialties", vol. 60, No. 9 (Sep., 1984), p. 90 (Liquid Toothpaste).
Household and Personal Products Industry, Sep. 1981, pp. 62–65.
Journal of the Society Cosmetic Chemists, vol. 21, pp. 459–470 (1970).
Cosmetics Science and Technology, Balsam and Sagarin, vol. 1, pp. 510–511 (1972).
Harry's Cosmeticology, 7th Edition, 1982, pp. 616–617.

Primary Examiner—Richard D. Lovering
Attorney, Agent, or Firm—Milton L. Honig

[57] ABSTRACT

The invention concerns a process for making a toothpaste containing an abrasive agent and a binder consisting wholly or partly of guar gum or other plant gum. The plant gum is hydrated by a liquid hydration medium consisting of water and 0 to 33% by weight of the hydration medium of sorbitol. To hydrate the plant gum it is mixed with the hydration medium in the presence of sufficient of the abrasive agent to produce enough shear to give a smooth cream. Other conventional ingredients are then mixed in.

12 Claims, 1 Drawing Sheet

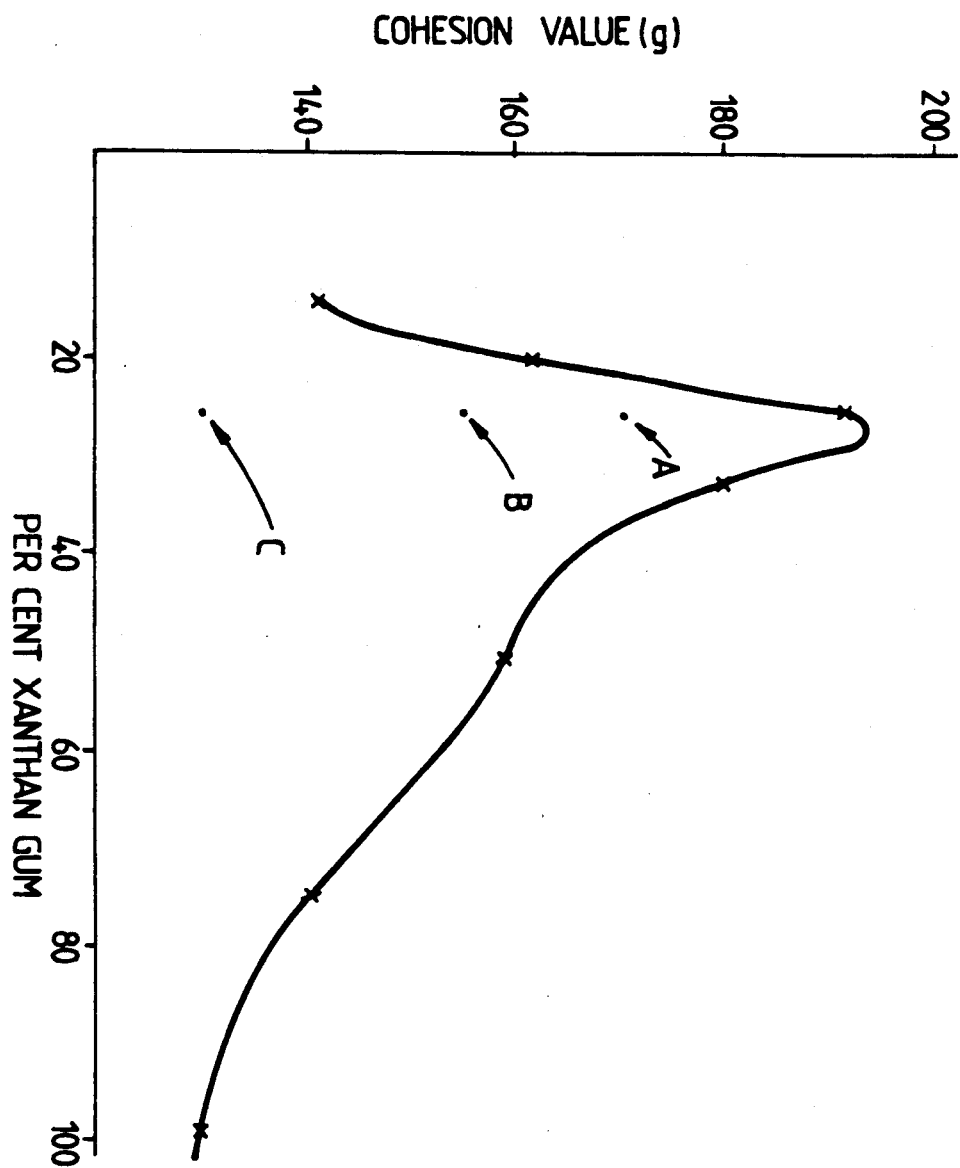

PROCESS FOR MAKING TOOTHPASTE

This is a continuation application of Ser. No. 930,461, filed Nov. 12, 1986, now abandoned.

This invention relates to a process for making toothpaste.

Most toothpastes consist of a suspension of a particulate cleaning agent in an aqueous humectant liquid phase. In order to hold the solid and liquid constituents in the form of a stable paste with desirable rheological properties the toothpaste invariably also includes a binder, sometimes referred to as a thickener. A large number of different binders have been suggested in the literature.

It has recently been suggested in GB-A-1 604 216 (Hercules) and GB-A-2 082 062 (Colgate-Palmolive) to use certain blends of xanthan gum and guar gum (or other galactomannan gum) as a binder system for toothpastes. However, the toothpaste formulator encounters certain difficulties in making a satisfactory toothpaste containing guar gum, whether used as sole binder or whether blended with xanthan gum or other binder. Such difficulties arise from the problem of making a toothpaste in which the guar gum has been hydrated satisfactorily. Unsatisfactory hydration of this binder leads to products having an unacceptable texture for a commercial product. The appearance of a toothpaste is one of its most important characteristics (see Household & Personal Products Industry, September 1981, page 62 and J.Soc Cosmet Chem. 21 459–470 [1970]). The extruded ribbon is required to be smooth, uniform and shiny in appearance.

EP-A-30 435 (Merck) refers to the difficulty of dispersing xanthan-guar gum blends in water and proposes the use of a glycol-treated xanthan gum for dry blending with the guar or other plant gum such as tara gum, locust bean gum and tamarind gum.

In the manufacture of toothpastes various methods have been suggested for effecting the hydration of the toothpaste binder. In "Cosmetics, Science & Technology", Balsam & Sagarin, 1972, Volume 1, pages 510 and 511 two general methods of toothpaste manufacture are described. In one method the binder is prewetted with the humectant and then dispersed in the liquid portion of the formulation. In the second method the binder is premixed with solid abrasives and introduced into a mixer simultaneously with an aqueous solution of the humectant. These two methods are recommended in GB-A-2 117 637 (Colgate-Palmolive) for the hydration of a binder blend of xanthan gum and sodium alginate. In "Harry's Cosmeticology", Seventh Edition, 1982, pages 616 and 617 reference is made to carrying out the hydration of the solid gelling agent by adding it to the humectant and part of the water under conditions of vigorous agitation. In U.S. Pat. No. 4,081,526 (Kao) the binder is dispersed in propylene glycol and then sorbitol and water are added to the dispersion and the mixture agitated. The procedure followed Example I of EP-A-97 476 (Procter & Gamble) involves forming a slurry of part of the sorbitol solution and two binders, Carbopol and xanthan gum, in one vessel and adding this to a pre-formed mixture of the remainder of the sorbitol solution and the other ingredients, including the water, in a separate vessel. A method described in GB-A-1 448 193 (Colgate-Palmolive) involves dispersing the gelling agent in a humectant, optionally with water also present, whereafter additional humectant and water, such as aqueous 70% sorbitol solution, may be mixed with the dispersion. The procedure referred to in U.S. Pat. No. 4,122,162 (Muhlemann et al) involves dissolving the binder in part of the water and then adding the other ingredients, the resulting mass being thoroughly mixed in a mixer.

Three procedures for combining dentifrice ingredients are described in an article entitled "How to formulate a dentifrice" by David Garlen published in Household & Personal Products Industry, September 1981, pages 62, 63 and 65. In the first procedure binder is sprinkled under agitation into humectant so that the particles are dispersed in the absence of water, preventing swelling at this point. To this is added a separate liquid phase which includes the available water. In the second procedure a hot solution of humectant and water is slowly added to a dry blend of the binder and abrasive. The third procedure is particularly for formulations using as binder system a mixture of Veegum and a carboxymethylcellulose. In this procedure the Veegum is added to hot water to which is added a separate phase consisting of the bulk of the humectant and the binder, followed by the balance of the humectant. Mixing under vacuum is then carried out.

Of the above disclosures that refer specifically to the use of mixtures of xanthan gum and guar gum in toothpastes, GB-A-1 604 215 (Hercules) does not refer to a method of making a toothpaste, and in GB-A-2 082 062 (Colgate-Palmolive) the xanthan-guar gum mixture is added to a pre-mix of humectant and water and heated to 35° C.-60° C. with subsequent addition of the other ingredients.

In GB-A-2 082 062 it is stated that glycerol is preferably not employed as the humectant. The file record indicates that when using glycerol rather than sorbitol the resulting product exhibits phase separation and is rheologically undesirable. In GB-B- 2 082 062 it is stated that the humectant consists essentially of sorbitol.

It is an object the invention to provide an improved process for making a toothpaste comprising a plant gum, especially guar gum, as a binder.

According to the present invention there is provided a process for making a toothpaste comprising an aqueous liquid humectant phase consisting essentially of an aqueous sorbitol solution thickened by a hydrated binder comprising a hydrated plant gum, and a water-insoluble particulate abrasive agent dispersed in the thickened liquid phase, wherein the process is characterised in that hydration of the plant gum is carried out by mixing under shear the plant gum with a liquid hydration medium consisting of water and 0 to 33% by weight of the liquid hydration medium of sorbitol, the mixing being carried out in the presence of such an amount of the particulate abrasive agent that sufficient shear is produced during the mixing to effect uniform hydration of the plant gum with the production of a smooth cream, whereafter there is blended with the hydrated plant gum any remaining water and humectant, any remaining abrasive, and other conventional ingredients, to produce the toothpaste.

In the prior processes of making toothpastes comprising water and sorbitol solution, the binder is frequently hydrated by dispersing it in a mixture of the available water and sorbitol solution. We have now found that the inclusion of substantial amounts of sorbitol in the hydration medium has a deleterious effect on the hydration of the plant gum, the final toothpaste having a granular texture giving a ribbon when extruded from a toothpaste tube which is rough and dull in appearance rather than smooth and shiny.

In the process of the invention the amount of sorbitol in the liquid hydration medium is preferably less than 25%, more preferably less than 20%, by weight of the liquid hydration medium.

Nevertheless, the inclusion in the liquid hydration medium of some sorbitol may sometimes be desirable. Toothpaste may tend to splash onto the side walls of the mixer during mixing and loss of the quality of the final toothpaste may result if this paste dries out and is subsequently mixed in. The presence of some sorbitol, say 1 to 5% by weight of the liquid hydration medium, is generally adequate to avoid this effect.

The process of the invention is applicable to the manufacture of toothpaste comprising a binder system made up of a plant gum in conjunction with another binder. Generally such combinations will comprise at least 10% by weight of the plant gum.

As noted above, the hydration of plant gums presents the toothpaste formulator with severe problems. These are due to the very high affinity of these gums for water. This property readily leads to the formation of lumps which are made up of an outer layer of swollen particles enclosing particles which are not hydrated and which the water cannot reach or can only reach very slowly. To effect satisfactory hydration, therefore, it is necessary to subject the mixture to high shear so as to break down these lumps and enable uniform hydration to take place. Unfortunately, conventional toothpaste mixers do not generate sufficient shear to give satisfactory hydration of plant gums. Even using the so-called high shear mixers, eg. the Fryma VME 120 mixer (supplied by Fryma, Switzerland) or Molteni TM5 mixer (supplied by Molteni, Milan, Italy), we have found that the shear produced is inadequate to result in the production of a smooth cream. These difficulties are overcome in the process of this invention by including in the mixer with the gum and the liquid hydration medium at least a part of the particulate abrasive agent. The Applicants have found that by this step it is possible to produce sufficient shear to effect uniform hydration of plant gums and produce a smooth cream even when employing conventional low-shear mixers such as the Thompson toothpaste mixer (supplied by Hobal Engineering, United Kingdom) or Lang VACUMIX mixer (supplied by Lang London, Middlesex, United Kingdom). The amount of particulate abrasive required to produce sufficient shear depends on the type of mixer used, greater amounts being necessary when low shear mixers are used. In general, the amount required when using the high shear mixers referred to above will be at least about 10% by weight of the toothpaste, and at least about 30% by weight in the case of the low shear mixers. In Applicants' process whilst the hydration of the binder can be carried out in a separate vessel this is not necessary and the whole process can be carried out more advantageously in the toothpaste mixer.

After the hydration of the plant gum, there is blended with the hydrated gum in a toothpaste mixer any remaining water, the liquid humectant or the remainder of it, the remainder of the abrasive, if any, additional binder if desired, and other conventional ingredients. Otherwise the further processing follows generally conventional procedures. Detergent and flavouring ingredients are usually the last ingredients to be incorporated.

Additional binder, if present, such as xanthan gum, is desirably hydrated after the plant gum has been hydrated, although hydration of the xanthan gum may be effected at the same time as the hydration of the plant gum. It is, however, preferable that ingredients which compete with the plant gum for the water of the liquid hydration medium are excluded from that medium.

In the toothpaste manufacturing process of this invention the toothpaste humectant employed consists essentially of sorbitol. Thus, the presence of minor amounts of other humectants still permitting the obtaining of satisfactory toothpaste products is contemplated.

It is known that the combination of a plant gum and xanthan gum when used to thicken water gives a synergistic thickening effect (Food Technology, March 1973 pages 26 to 30). When the viscosity is plotted against the xanthan: plant gum weight ratio the curve passes through a maximum. The Applicants have now discovered that a synergistic effect can also be obtained in the case of toothpastes, but that this effect does not depend solely on the relative proportions of the two gums but also depends on the amount of sorbitol in the liquid hydration medium. The synergistic thickening effect decreases as the proportion of sorbitol increases, and eventually disappears. In the process of the invention the amount of sorbitol in the liquid hydration medium is at most 33%, and is preferably at most 25%, and more preferably does not exceed 20% by weight of the liquid hydration medium. For toothpastes made in accordance with the present invention and containing xanthan gum as a second binder a synergistic thickening has been obtained over the xanthan:guar gum weight range 6:1 to 1:6, especially 3:2 to 1:4, the cohesion values of the toothpastes passing through a maximum between these ratios. Thus by the use of the process of the present invention for manufacturing toothpastes comprising a binder mixture of a plant gum, especially guar gum, and xanthan gum a more cost effective use of the gums is obtainable.

A wide variety of particulate abrasive agents may be employed in the manufacture of toothpastes according to this invention. Examples of such materials are hydrated alumina, silica, water-insoluble sodium metaphosphate, tricalcium phosphate, calcium phosphate dihydrate, anhydrous dicalcium phosphate, calcium pyrophosphate, calcium carbonate and aluminium silicate. Mixtures of abrasive agents may be used. Toothpaste abrasive agents generally have an average particle size between 1 and 30 microns. In order to provide acceptable cleaning power toothpastes generally comprise in practice between 5 and 60% by weight of abrasive agent.

The amount of binder included in toothpastes made according to the invention will usually be in the range 0.2 to about 2% by weight of the toothpaste. The amount of sorbitol, expressed as 70% aqueous solution, will generally be from 20 to 75% by weight of the toothpaste.

Toothpaste made according to the process of the invention may include various well-known optional ingredients such as a fluoride or monofluorophosphate, whitening agent, preservative, sweetener, antibacterial agent, flavour and pH-adjusting agent.

The following Examples illustrate the invention. Percentages are by weight.

EXAMPLE 1

A number of toothpastes were made according to the following general formula.

|  | % |
| --- | --- |
| Alumina trihydrate | 50.00 |
| Sorbitol syrup (70% solution) | 27.00 |
| Guar gum } | 0.70 |
| Xanthan gum |  |
| Saccharin | 0.20 |
| Monosodium phosphate | 0.30 |
| Sodium monofluorophosphate | 0.82 |
| Formalin | 0.04 |
| Titanium dioxide | 1.00 |
| Sodium lauryl sulphate | 1.50 |
| Sodium dodecylbenzene sulphonate | 0.50 |
| Flavour | 1.00 |
| Water | 16.94 |

Various toothpastes were made in which the guar gum:xanthan gum weight ratio was varied.

These toothpastes were made by the following process. The toothpastes were made in 3 kilogram quantities in a low shear Lang VACUMIX toothpaste mixer in the following stages. Mixing was carried out under vacuum.

Stage 1

508.20 g water are put in the mixer.

Stage 2

The guar gum is dry mixed with 1000 g alumina trihydrate and drawn into the mixer. Mixing takes place for about 10 minutes. A smooth cream is produced.

Stage 3

In a separate vessel the following ingredients are mixed

| Sorbitol syrup | 510.00 g |
| --- | --- |
| Saccharin | 6.00 g |
| Monosodium phosphate | 9.00 g |
| Sodium monofluorophosphate | 24.60 g |
| Formalin | 1.20 g |

The mixer is heated to dissolve all the solid ingredients in the sorbitol syrup. The solution is slowly drawn into the mixer and mixed for 10 minutes.

Stage 4

A dry mix of the remainder of the alumina trihydrate, 500.00 g, the titanium dioxide 30.00 g and the xanthan gum, 5.25 g, is slowly drawn into the mixer and mixed for about 15 minutes.

Stage 5

A mixture of the detergents (45.00 g sodium lauryl sulphate and 15.00 g sodium dodecylbenzene sulphonate) in the remainder of the sorbitol syrup, 300.00 g, is drawn into the main mixer and mixed for 15 minutes.

Stage 6

The flavour, 30.00 g, is drawn in and mixing for 10 minutes carried out.

The toothpaste is then packed into tubes.

The cohesion values (g) of the toothpastes were determined 24 hours after manufacture. The cohesion value is a measure of the consistency of a toothpaste (see J. Soc. Cosmet. Chem. 21 459–470 (1970) at page 461) and is determined using an instrument which measures the force required to pull apart a standard volume of toothpaste between plates of standard area.

The results are illustrated in the attached drawing which shows a plot of the cohesion value against the percentage xanthan gum in the binder combination, the balance being guar gum. The curve shows that a marked synergistic effect is obtained between xanthan:guar weight ratios of 6:1 to 1:6, more especially between 3:2 to 1:4.

On the drawing is also plotted the 24 hr cohesion values of toothpaste having a xanthan:guar gum weight ratio of 1:3 which were made by modifying the process described above to include varying amounts of the sorbitol syrup with the water in Stage 1. The points A, B & C correspond, respectively, to the incorporation into the mixer at Stage 1 of 150 g, 450 g and 810 g sorbitol syrup, the liquid hydration medium (ie. water+sorbitol syrup) containing, respectively, 16.0%, 32.9% and 43.0% sorbitol.

It is seen that there is no synergistic increase in the cohesion value when all the sorbitol syrup (810 g) is included in the liquid hydration medium.

The toothpastes corresponding to the points on the curve and also points A and B had a satisfactory smooth texture and acceptable appearance. The toothpaste corresponding to point C, which is not made by a process according to this invention, had a rough granular texture. The coarse texture of the toothpaste ribbon, especially noticeable when spread with the finger, meant that the product was of poor quality. The toothpaste ribbon lacked that uniformly smooth texture required of an acceptable commercial product.

The above described procedure for carrying out the process of this invention can also be performed using other toothpaste mixers, for instance, Thompson or Fryma mixers.

Several variations of stages 3 and 4 are also possible without any substantial change in the properties of the resultant toothpastes. For instance, the sequence of these stages may be reversed. The electrolyte added in Stage 3 could alternatively be dissolved in the water of Stage 1.

When glycerol is substituted for the sorbitol syrup an unsatisfactory product is obtained. Phase separation occurs on storage.

EXAMPLE 2

A toothpaste was made according to the formula and process of Example 1 except that the guar gum in Stage 2 was replaced by 21 g of the commercial blend of guar gum and xanthan gum referred to in Comparative Example A and no xanthan gum was added at Stage 4.

A satisfactory toothpaste giving an extruded ribbon of smooth texture and acceptable appearance was obtained.

EXAMPLE 3

A toothpaste was made according to the following formula.

|  | % |
| --- | --- |
| Alumina trihydrate | 30.00 |
| Precipitated silica | 9.00 |
| Sorbitol syrup (70% solution) | 15.00 |

-continued

| | % |
|---|---|
| Guar gum | 1.00 |
| Saccharin | 0.20 |
| Monosodium phosphate | 0.30 |
| Sodium monofluorophosphate | 0.82 |
| Formalin | 0.04 |
| Titanium dioxide | 1.00 |
| Sodium lauryl sulphate | 2.10 |
| Flavour | 0.90 |
| Water | 39.64 |

This toothpaste was made in a 5 kilogram quantity in a Molteni TM5 mixer in the following stages. Mixing was carried out under vacuum.

Stage 1

Water (1825 g) and sorbitol syrup (250 g) were put in the mixer. Then saccharin (10 g), monosodium phosphate (15 g), sodium monofluorophosphate (41 g) and formalin (2 g) were added and mixed for 5 minutes.

Stage 2

The guar gum (50 g) and titanium dioxide (50 g) were dry mixed with alumina trihydrate (1500 g) and then drawn into the mixer. Mixing took place for about 20 minutes.

Stage 3

Sorbitol syrup (250 g) was drawn into the mixer and mixing took place for 5 minutes.

Stage 4

The precipitated silica (450 g) was drawn into the mixer. Mixing takes place for 15 minutes.

Stage 5

The sodium lauryl sulphate (105 g) was dissolved in the remainder of the water (157 g) and sorbitol syrup (250 g), and drawn into the mixer and mixed for 15 minutes.

Stage 6

The flavour (45 g) was drawn in and mixed for 10 minutes.

The toothpaste was then packed into tubes. Extruded toothpaste had a satisfactory smooth texture and acceptable appearance.

Comparative Example A

A toothpaste was made by the process of Example 1 save that all the sorbitol syrup was included at Stage 1; at Stage 2 the guar gum was replaced by 25.5 g a commercial blend of guar gum and xanthan gum (weight ratio 92.5:7.5) available commercially from Hercules Inc. as DP 4-33 (see Example 1 of GB-A-2 082 062); and at Stage 4 no xanthan gum was included. The resulting toothpaste was of poor quality. The toothpaste ribbon had a dull appearance and had a rough granular texture.

Comparative Example B

The process of Example 1 was repeated save that all the alumina trihydrate was included at Stage 4 and none at Stage 2. The resulting pastes were unsatisfactory in appearance having a rough granular texture. At Stage 2 a smooth cream was not obtained, there being present lumps indicative of incompletely hydrated binder.

Comparative Example C

In this comparative example toothpastes having the formula of Example 1 were made utilising features of the process described in GB-A-2 082 062 (Colgate-Palmolive).

In Stage 1 of the process all the sorbitol syrup was included with the water. In Stage 2, a mixture of guar gum and xanthan gum was used and the abrasive omitted, all the abrasive being added at Stage 4. During Stage 2, the mixture was heated to 60° C.

The xanthan gum:guar gum weight ratio was varied.

All the toothpastes had an unacceptable rough granular texture and the cohesion values obtained showed no synergistic peak in the range 1:6:1:1 for the xanthan:guar weight ratio. Typical values obtained were as follows:

| Weight ratio xanthan:guar | 24 hr cohesion value (g) |
|---|---|
| 1:6 | 220 |
| 1:4 | 200 |
| 1:3 | 170 |
| 1:1 | 130 |

Comparative Example D

A toothpaste was made having the following composition.

| | |
|---|---|
| Sorbitol syrup (70% solution) | 23.000 |
| Xanthan-guar gum (DP 4-33) | 1.400 |
| Saccharin | 0.140 |
| Water | 22.683 |
| Alumina trihydrate | 45.000 |
| Titanum dioxide | 0.400 |
| Ascorbic acid | 0.400 |
| Sodium monofluorophosphate | 0.620 |
| Sodium lauryl (3-ethoxylated) sulphate (28% solution) | 5.357 |
| Flavour | 1.000 |

This formula is essentially the same as that in Example 1 of GB-A-2 082 062 and differs only in that a different abrasive and fluoride is used.

The toothpaste was made in a 3 kg quantity.

In the first stage the xanthan-guar gum was combined with all the water and sorbitol under conditions of vigorous agitation at 60° C. Since all the water and sorbitol was used at this stage, the saccharin, ascorbic acid and sodium monofluorophosphate were dissolved in the liquids prior to addition of the binder gum mixture. When the DP 4-33 had been dispersed in the liquids, the mixture was transferred to a 3 kg Lang mixer and the remaining ingredients, abrasive, detergent and flavour, were drawn in one at a time with mixing after each addition.

Great difficulty was experienced in satisfactorily hydrating the gums at the first stage. In an attempt to avoid the presence of lumps in the final product, the mixing was carried out using a high shear homogenizer for 1 hour (although such a lengthy procedure would be quite unacceptable in commercial practice). Although by this means it was possible to produce a final toothpaste free of lumps, the toothpaste had a coarse granular texture which became worse after 24 hours. Thus even under the extreme mixing conditions described a satisfactory toothpaste was not obtained.

I claim:

1. A process for making a toothpaste comprising an aqueous liquid humectant phase consisting essentially of an aqueous sorbitol solution thickened by a hydrated binder comprising a hydrated plant gum, which is guar gum, and a water-insoluble particulate abrasive agent dispersed in the thickened liquid phase, said process comprising the steps of:
   a) hydrating the plant gum by mixing the gum under shear with a liquid hydration medium consisting of water and from 1 to less than 25% by weight of the liquid hydration medium of sorbitol, the mixing being conducted in the presence of an amount of particulate abrasive agent in an effective amount to produce sufficient shear during the mixing to effect uniform hydration of the plant gum with production of a smooth cream; and
   b) blending the hydrated plant gum resulting from step (a) with a further amount of sorbitol, any remaining water, any remaining abrasive and other conventional ingredients, to produce the toothpaste.

2. A process as claimed in claim 1, wherein the liquid hydration medium comprises less than 25% sorbitol by weight of the medium.

3. A process as claimed in claim 1, wherein the hydration of the plant gum is carried out in the presence of at least 10% by weight of the toothpaste of the particulate abrasive agent.

4. A process as claimed in claim 3, wherein the hydration of the plant gum is carried out in the presence of at least 30% by weight of the toothpaste of the particulate abrasive agent.

5. A process as claimed in claim 1 wherein the amount of binder is 0.2 is 2% by weight of the toothpaste.

6. A process as claimed in claim 1 wherein the amount of sorbitol, expressed as 70% aqueous solution, is 20 to 75% by weight of the toothpaste.

7. A process as claimed in claim 1 wherein the water-insoluble particulate abrasive agent is hydrated alumina or silica or a mixture thereof.

8. A process for making a toothpaste comprising an aqueous liquid humectant phase consisting essentially of an aqueous sorbitol solution thickened by a hydrated binder comprising a hydrated plant gum, which is guar gum, and also hydrated xanthan gum, and a water-insoluble particulate abrasive agent dispersed in the thickened liquid phase, said process comprising the steps of:
   a) hydrating the plant gum by mixing the gum under shear with a liquid hydration medium consisting of water and from 1 to less than 25% by weight of the liquid hydration medium of sorbitol, the mixing being conducted in the presence of an amount of particulate abrasive agent in an effective amount to produce sufficient shear during the mixing to effect uniform hydration of the plant gum with production of a smooth cream; and
   b) blending the hydrated plant gum resulting from step (a) with a further amount of sorbitol, and any remaining water, any remaining abrasive and other conventional ingredients, to produce the toothpaste.

9. A process as claimed in claim 8 wherein hydration of the xanthan gum is effected after the hydration of the plant gum.

10. A process as claimed in claim 5 wherein hydration of the xanthan gum is effected at the same time as the hydration of the plant gum.

11. A process as claimed in claim 8 wherein the weight ration of xanthan gum to guar gum is 6:1 to 1:6.

12. A process as claimed in claim 11 wherein the weight ratio of xanthan gum to guar gum is 3:2 to 1:4.

* * * * *